United States Patent
Shirazian et al.

(10) Patent No.: US 12,424,332 B2
(45) Date of Patent: Sep. 23, 2025

(54) UNIFIED ANISOTROPIC VOLUME AND SURFACE MESH STORAGE

(71) Applicant: Intuitive Surgical Operations, Inc., Sunnyvale, CA (US)

(72) Inventors: Pourya Shirazian, Sunnyvale, CA (US); Mahdi Azizian, Santa Clara, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

(21) Appl. No.: 18/600,308

(22) Filed: Mar. 8, 2024

(65) Prior Publication Data
US 2024/0212863 A1 Jun. 27, 2024

Related U.S. Application Data

(63) Continuation of application No. 16/627,171, filed as application No. PCT/US2018/039613 on Jun. 26, 2018, now Pat. No. 11,955,246.

(Continued)

(51) Int. Cl.
| | |
|---|---|
| *G16H 50/50* | (2018.01) |
| *A61B 5/055* | (2006.01) |
| *A61B 6/03* | (2006.01) |
| *A61B 8/00* | (2006.01) |
| *G06T 15/80* | (2011.01) |
| *G06T 17/20* | (2006.01) |

(52) U.S. Cl.
CPC ............. *G16H 50/50* (2018.01); *A61B 5/055* (2013.01); *A61B 6/032* (2013.01); *A61B 8/485* (2013.01); *G06T 15/80* (2013.01); *G06T 17/20* (2013.01); *G06T 2210/41* (2013.01)

(58) Field of Classification Search
CPC ........... A61B 6/032; A61B 5/055; A61B 8/00; A61B 2034/101; A61B 2090/374; G06T 2207/30004; G06T 15/80; G06T 17/205; G06T 15/205; G06T 2215/12; G06T 7/162; G06T 7/507
See application file for complete search history.

(56) References Cited

U.S. PATENT DOCUMENTS

| | | |
|---|---|---|
| 6,313,837 B1 | 11/2001 | Assa et al. |
| 6,714,901 B1 | 3/2004 | Cotin et al. |

(Continued)

OTHER PUBLICATIONS

Arnab 2009 PhD. Thesis Dept of Engineering University of Warwick UK 269 pages (Year: 2009).*

(Continued)

*Primary Examiner* — Keith M Raymond
*Assistant Examiner* — Patrick M Mehl
(74) *Attorney, Agent, or Firm* — Foley & Lardner LLP

(57) ABSTRACT

A method is provided to model a 3D structure comprising: producing a surface mesh representation of the 3D structure; producing a volume mesh representation of the 3D structure based upon the surface mesh; sorting vertices of the volume mesh into a first sub-list that includes only surface vertices and a second sub-list that includes only internal vertices; applying shading to the surface mesh by accessing only surface vertices in the first sub-list; determining deformation of the volume mesh by accessing both surface vertices in the first sub-list and internal vertices in the second sub-list.

20 Claims, 15 Drawing Sheets

| | Nodes | Colors | Normals | Masses | Youngs Modulo | Poison Rate |
|---|---|---|---|---|---|---|
| Surface | $P_0$ | $C_0$ | $N_0$ | $M_0$ | $Y_0$ | $O_0$ |
| | $P_1$ | $C_1$ | $N_1$ | $M_1$ | $Y_1$ | $O_1$ |
| | $P_2$ | $C_2$ | $N_2$ | $M_2$ | $Y_2$ | $O_2$ |
| | ⋮ | ⋮ | ⋮ | ⋮ | ⋮ | ⋮ |
| | $P_{15}$ | $C_{15}$ | $N_{15}$ | $M_{15}$ | $Y_{15}$ | $O_{15}$ |
| Internal | $Q_0$ | | | $M'_0$ | $Y'_0$ | $O'_0$ |
| | $Q_1$ | | | $M'_1$ | $Y'_1$ | $O'_1$ |
| | $Q_2$ | | | $M'_2$ | $Y'_2$ | $O'_2$ |
| | ⋮ | | | ⋮ | ⋮ | ⋮ |
| | $Q_{15}$ | | | $M'_{15}$ | $Y'_{15}$ | $O'_{15}$ |

Related U.S. Application Data

(60) Provisional application No. 62/526,231, filed on Jun. 28, 2017.

(56) References Cited

U.S. PATENT DOCUMENTS

| | | | |
|---|---|---|---|
| 11,826,133 | B2 | 11/2023 | Huang |
| 2005/0219245 | A1 | 10/2005 | Tao et al. |
| 2006/0290695 | A1 | 12/2006 | Salomie et al. |
| 2007/0109299 | A1 | 5/2007 | Peterson et al. |
| 2011/0040169 | A1 | 2/2011 | Kamen et al. |
| 2012/0038639 | A1 | 2/2012 | Mora et al. |
| 2014/0085312 | A1 | 3/2014 | Garg et al. |
| 2014/0226884 | A1 | 8/2014 | Porikli et al. |
| 2017/0116779 | A1 | 4/2017 | Lalish et al. |
| 2020/0161004 | A1 | 5/2020 | Shirazian et al. |

OTHER PUBLICATIONS

Hahn et al. 2013 Proc. 12th ACM SIGGRAPH:ESCA 2013 165-171 (Year: 2013).*

Kartasheva et al. 2003 J. Comp. Info. Sci. Engin. 3:285-294 (Year: 2003).*

Wikibooks 2017 Blender 3D:Noob to Pro advanced tutorials internet address via wayback machine stamped Jan. 7, 2017 https://web.archive.org/web/20170107030312/https://en.wikibooks.org/wiki/Blender_3D:_Noob_to_Pro/Advanced_Tutorials/Advanced_Animation/Guided_tour/Mesh/vg 5 pages (Year: 2017).*

Arnab 2009 PhD., Thesis Dept of Engineering University of Warwick UK 269, 269 pages.

Extended European Search Report for Application No. 18823537.8 mailed on Nov. 2, 2020, 9 pages.

Hahn F., et al., "Efficient Simulation of Secondary Motion in Rig-Space," Proceedings of the 2013 ACM SIGGRAPH:ESCA, Jul. 2013, pp. 165-171.

International Preliminary Report on Patentability for Application No. PCT/US2018/039613, mailed on Jan. 9, 2020, 11 pages.

International Search Report and Written Opinion for Application No. PCT/US2018/039613, mailed on Nov. 7, 2018, 14 pages (ISRG09790/PCT).

Kartasheva E., et al., "Surface and Volume Discretization of Functionally Based Heterogeneous Objects," Computing and Information Science in Engineering, Dec. 2003, vol. 3(4), pp. 285-294.

Khalifah A., and Roberts D., "Survey of Modelling Approaches for Medical Simulators," 2004, 9 pages.

Pan L., et al., "An Improved Facial Orthopedic Surgery Planning System with Pre-processing FEM Modeling," 18th International Conference on Artificial Reality and Telexistence, 2008, pp. 116-122.

Rungta S., et al., "A Comparative Analysis of New Approach With an Existing Algorithm to Detect Cycles in a Directed Graph," ICT and Critical Infrastructure: Proceedings of the 48th Annual Convention of Computer Society of India, 2014, vol. 2, pp. 37-47.

Vertut, J., and Coiffet, P., "Robot Technology: Teleoperation and Robotics Evolution and Development," English translation, Prentice-Hall, Inc., Inglewood Cliffs, NJ, USA 1986, vol. 3A, 332 pages.

Wagner D.W., et al., "Deriving Tissue Density and Eelastic Modulus from MicroCT Bone Scans, "Bone, 2011, vol. 49(5), pp. 931-938.

Wikibooks 2017 Blender 3D:Noob to Pro advanced tutorials internet address via wayback machine stamped Jan. 7, 2017 https://web.archive.org/web/20170107030312/https://en.wikibooks.org/wiki/Blender_3D:_Noob_to_Pro/Advanced_Tutorials/Advanced_Animation/Guided_tour/Mesh/vg 5 pages; last modified Jul. 2016 (Year: 2016).

Wikipedia, "Viscoelasticity," downloaded Nov. 10, 2020, 10 pages, Retrieved from the Internet : http://en.wikipedia.org/w/index.php?title=Viscoelasticity&oldid=779774681.

Extended European Search Report for Application No. EP24202886.8, mailed on Dec. 9, 2024, 11 pages.

* cited by examiner

| | Nodes | Colors | Normals | Masses | Youngs Modulo | Poison Rate |
|---|---|---|---|---|---|---|
| Surface | $P_0$ | $C_0$ | $N_0$ | $M_0$ | $Y_0$ | $O_0$ |
| | $P_1$ | $C_1$ | $N_1$ | $M_1$ | $Y_1$ | $O_1$ |
| | $P_2$ | $C_2$ | $N_2$ | $M_2$ | $Y_2$ | $O_2$ |
| | ⋮ | ⋮ | ⋮ | ⋮ | ⋮ | ⋮ |
| | $P_{15}$ | $C_{15}$ | $N_{15}$ | $M_{15}$ | $Y_{15}$ | $O_{15}$ |
| Internal | $Q_0$ | | | $M'_0$ | $Y'_0$ | $O'_0$ |
| | $Q_1$ | | | $M'_1$ | $Y'_1$ | $O'_1$ |
| | $Q_2$ | | | $M'_2$ | $Y'_2$ | $O'_2$ |
| | ⋮ | | | ⋮ | ⋮ | ⋮ |
| | $Q_{15}$ | | | $M'_{15}$ | $Y'_{15}$ | $O'_{15}$ |

FIG. 6

UNIFIED ANISOTROPIC VOLUME AND SURFACE MESH STORAGE

CROSS-REFERENCE TO RELATED APPLICATIONS

This application is a continuation of U.S. application Ser. No. 16/627,171, filed on Dec. 27, 2019, which is a U.S. National Stage Filing under 35 U.S.C. 371 from International Application No. PCT/US2018/039613, filed on Jun. 26, 2018, and published as WO2019/005881 A1 on Jan. 3, 2019, which claims the benefit of and priority to U.S. Provisional Patent Application Ser. No. 62/526,231, filed on Jun. 28, 2017, all of which are incorporated herein by reference in its entirety.

BACKGROUND

A volume mesh is a representation of the interior volume of an object. A volume mesh may be used to simulate surface and volume deformation due to external forces through finite element analysis, for example. In a physically-based simulation, a volume mesh model of a physical object ordinarily includes a grid of tetrahedral or hexahedral elements that aids in the computation of deformations to the volume mesh due to virtual forces imparted to the volume mesh. A volume mesh, however, generally does not capture shading material and the outer texture of the simulated object as viewed under a light source. To this end, a surface mesh may be added to support the computation of light interactions with a boundary surface of the volume mesh i.e. through material shading. However, displacement of surface portions of the volume mesh during simulation must be propagated to the surface mesh for material shading to account for these surface deformations during the simulation. A process to propagate volumetric changes to a surface has used manual definition of multiple anchor points on a surface mesh to synchronize motion between the volumetric mesh and the surface mesh during simulation. The anchor points propagate changes in position of a surface portion of a volume mesh during simulation to a surface mesh for use shading.

SUMMARY

A volume mesh represents a three-dimensional (3D) structure. The volume mesh includes a surface mesh portion. The volume mesh is made up of a multiplicity of polygons that each includes multiple vertices. Some of the vertices are surface vertices within the surface mesh portion and others are internal vertices. The vertices of the volume mesh are arranged in a list structure that includes a first sub-list that includes the surface vertices and that includes a second sub-list that includes the internal vertices. During shading, only the surface vertices in the first sub-list are accessed. During simulation involving application of virtual force to the volume mesh, both the surface vertices in the first sub-list and the internal vertices in the second sub-list are accessed.

In one aspect, a method of modeling a 3D structure is provided. A surface mesh is produced that represents the 3D structure. A volume mesh representation of the 3D structure is produced based upon the surface mesh. Vertices of the volume mesh are into a first sub-list that includes only surface vertices and a second sub-list that includes only internal vertices. Shading is applied to the surface mesh by accessing only surface vertices in the first sub-list. Deformation of the volume mesh is determined by accessing both surface vertices in the first sub-list and internal vertices in the second sub-list.

In another aspect, a data storage and retrieval system is provided for a computer memory. A computing system is configured to sort surface vertices and internal vertices of a volume mesh structure that represents a three-dimensional (3D) model to configure the memory according to a unified mesh structure. The unified mesh structure includes a first list including 3D locations of surface vertices of the volume mesh structure and includes a second list including 3D locations of internal vertices of the volume mesh structure.

BRIEF DESCRIPTION OF THE DRAWINGS

FIG. 6 is an illustrative drawing representing certain details of a unified mesh format representation of the volume mesh of FIG. 5.

DESCRIPTION OF EMBODIMENTS

Figure 1:
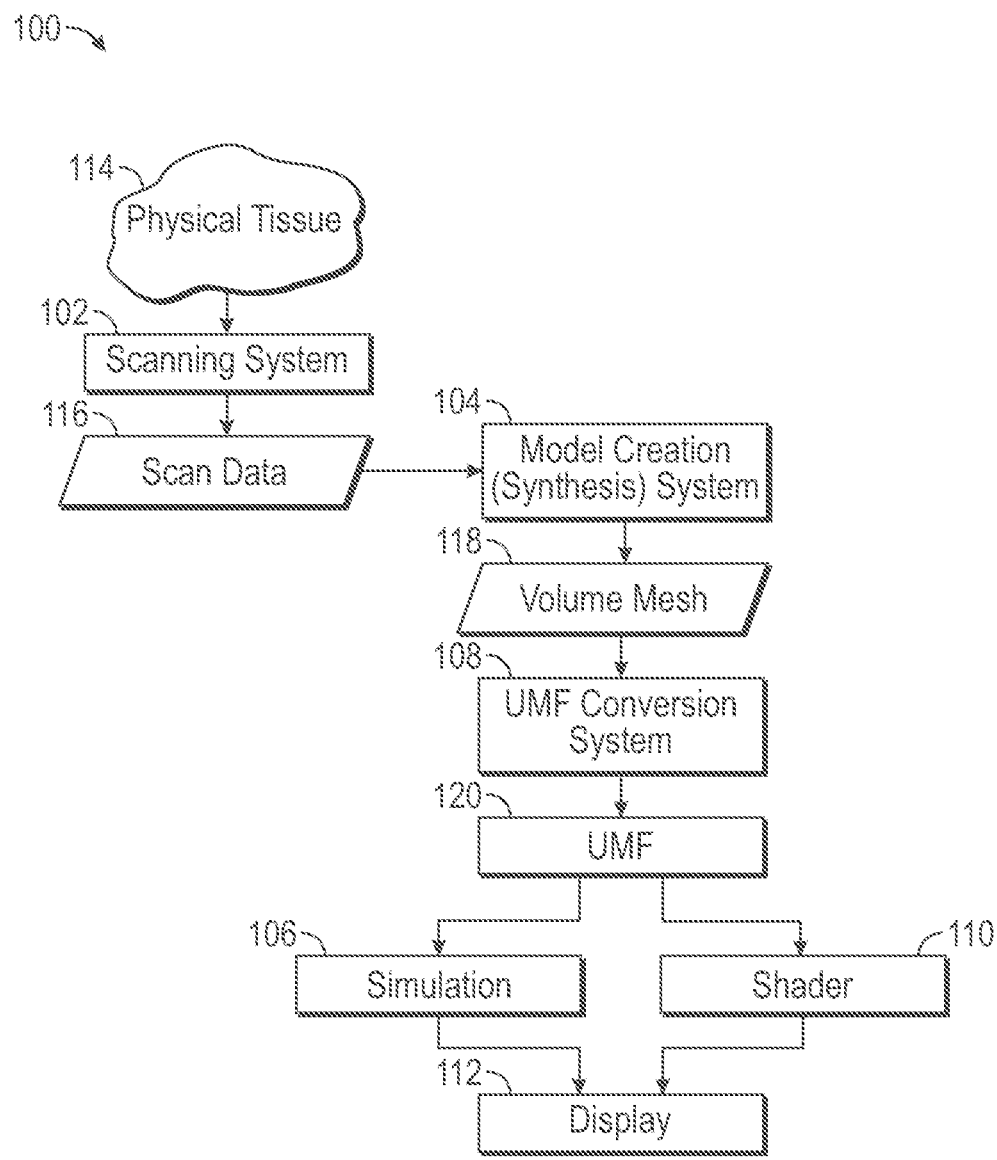
FIG. 1 is an illustrative drawing representing a simulation and shader system in accordance with some embodiments.

FIG. 1 is an illustrative drawing representing a simulation and shading system 100 in accordance with some embodiments. The system 100 includes a scanning system 102, a model creation (synthesis) engine 104, a model simulation engine 106, a conversion system 108, a shader engine 110 and a display system 112. The scanning system 102 is operative to scan the physical anatomical tissue object 114 to produce a three-dimensional (3D) image scan data model 116 that includes a three-dimensional image representation of the anatomical tissue object 114. The scanning system 102 may be implemented using any of a number of different modalities such as, Computerized Tomography (CT), Magnetic Resonance Imaging (MRI) or Ultrasound techniques, for example. The scanning system 102 produces image scan data 116 that indicates the physical tissue constituency at discreet three-dimensional volumetric locations within the tissue structure of the anatomical object 110. The model creation engine 104 produces a volume mesh structure 118, based upon the 3D image scan data model 116, to represent the physical anatomical tissue object 114 during a simulation. The conversion system 108 converts the volume mesh representation 118 to a unified mesh format (UMF) 120 in which surface vertices and internal vertices of polygons of the volume mesh representation 118 are separately grouped. The simulation engine 106 simulates application of real physical forces to impart real physical deformation to the real physical anatomical object 114, based upon the UMF representation 120 of the object 114, by applying virtual forces to deform a volume mesh representation 118. The shader engine 110 produces a (close to) photorealistic visual representation of a deformation of the object 114 based upon surface deformation of the volume mesh representation 118, to for display by the display system 112.

Figure 2:
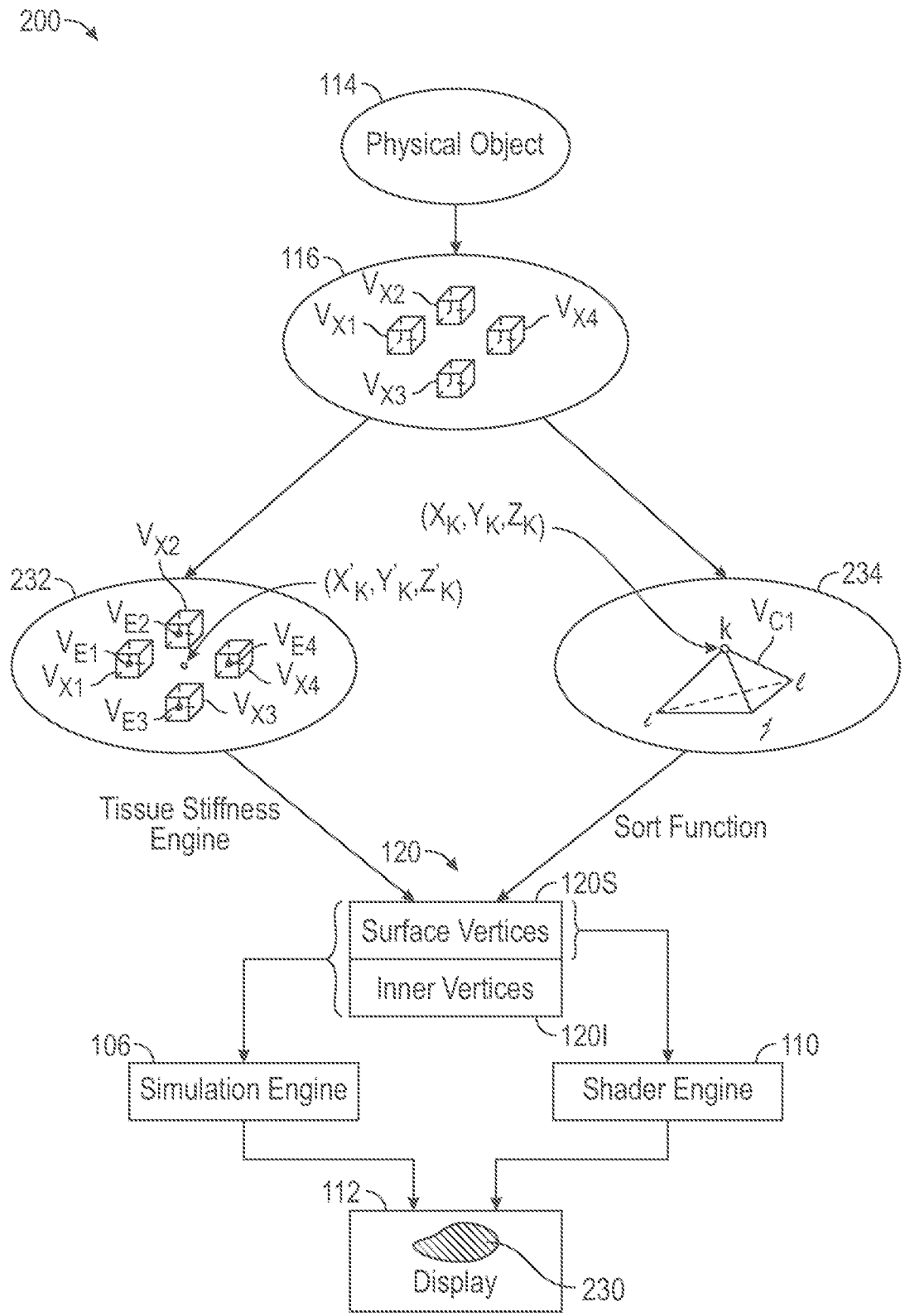
FIG. 2 is an illustrative generalized functional flow diagram representing showing certain data transformations performed by the system of FIG. 1 in the course of creating and using a unified mesh format (UMF) in accordance with some embodiments.

FIG. 2 is an illustrative generalized functional flow diagram representing a data method 200 to transform a three-dimensional (3D) image scan data model 116 of an object 114 to a UMF 120 and to use the UMF 120 to display an image 230 representing deformation of the 3D model 116 of the object 114. The method 200 may be performed by the system 100 of FIG. 1. The physical anatomical tissue object 114 is provided that may be a human organ such as a kidney, for example. A 3D image scan data model 116 is produced that provides a three-dimensional representation of the object 114. The 3D image scan data model 116 includes pixel data (pixels) arranged in a voxel grid in which pixels are disposed at voxel vertices. The illustrative diagram of FIG. 2 shows four example voxels $V_{x1}$-$V_{x4}$, each with eight vertices, each vertex associated with a pixel value (not shown). A viscoelasticity map 232 is produced based upon the 3D image scan data model 116 in which viscoelasticity values are associated with three-dimensional locations that correspond to locations within the image data set. The illustrative diagram of FIG. 2 shows four example viscoelasticity values $V_{E1}$-$V_{E4}$, each associated with one of the four example voxels $V_{x1}$-$V_{x4}$. Each voxel value represents viscoelasticity value for its entire voxel, which is computed based upon values of the eight voxels at the voxel's eight vertices. A volume mesh 234 also is produced based upon the 3D image scan data model 116 in which vertices of primitive volumetric cells that form the volume mesh are associated with three-dimensional locations that correspond to locations within the image data set. The illustrative diagram of FIG. 2 shows an example primitive tetrahedral volumetric cell $V_{C1}$ with four vertices (i, j, k, l).

It will be appreciated that because the 3D image scan data model 116 is produced based upon the physical object 114, three-dimensional locations within the image scan data model 116 correspond to three-dimensional locations within the physical object 114. Moreover, because both the viscoelasticity map 232 and the volume mesh 234 are produced based upon the image scan data model 116, 3D locations within the viscoelasticity map 232, correspond to 3D locations within the volume mesh 234. Furthermore, 3D locations within the viscoelasticity map 232 and corresponding 3D locations within the volume mesh 234 correspond to 3D locations within the physical object 114.

A vertex k of the example primitive volumetric cell $V_{C1}$ is disposed at 3D location ($x_k$, $y_k$, $z_k$) within the volume mesh 234, which corresponds to a 3D location ($x_k'$, $y_k'$, $z_k'$) within the viscoelasticity map 232. The location ($x_k'$, $y_k'$, $z_k'$) within the viscoelasticity map 232 is nearby to voxels $V_{x1}$-$V_{x4}$ within the viscoelasticity map 232. A tissue stiffness function determines a viscoelasticity value $V_{Ek}$ associated with the 3D location ($x_k'$, $y_k'$, $z_k'$) based upon the viscoelasticity values $V_{E1}$-$V_{E4}$ associated with nearby voxels $V_{x1}$-$V_{x4}$. A sorting function sorts vertices of primitive volumetric cells within the volume mesh 234, including the vertex k of volumetric cell $V_{C1}$ at location ($x_k$, $y_k$, $z_k$), into a UMF structure 120 in which surface vertices are grouped separately from internal vertices. The determined viscoelasticity value $V_{Ek}$ is stored in association with vertex k of volumetric cell $V_{C1}$ within the unified (surface and internal) mesh structure 120. Thus, the UMF 120 associates volumetric cell vertices with viscoelasticity values, e.g., associates vertex k with volumetric value $V_{Ek}$.

During simulation, a simulation engine 106 changes 3D locations of vertices of primitive volumetric cells within the volume mesh 232 in response to virtual forces to simulate deformation of the real physical object 114 in response to real forces. Simulation, therefore, results in updating of 3D locations of vertices within the UMF 120. A simulation image 230 is displayed on a computer display screen 112. A shader engine 110 uses color and texture information to produce a more realistic image 230 based upon the angle of incidence of light rays within a simulation scene upon vertices disposed at the surface of the volume mesh. The shader engine uses three-dimensional positions of vertices disposed at the surface of the volume mesh 232 to determine the vertex positions and orientation relative to light rays. A separate grouping of surface vertices 120S and internal vertices 120I within the UMF 120 makes the surface vertices easily available to the shader engine 110 while also making both the surface vertices 120S and the internal vertices 120I easily available to the simulation engine 106.

Figure 3A:
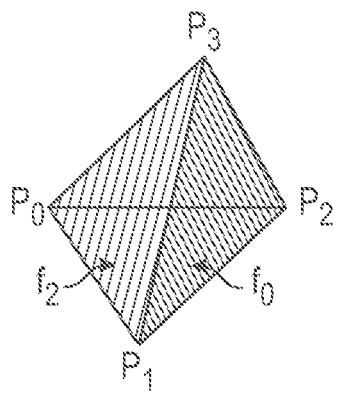
FIG. 3A-3C are illustrative perspective views of an example primitive tetrahedral volumetric cell.
Figure 3B:
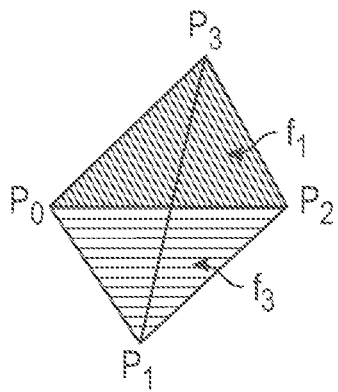
Figure 3C:
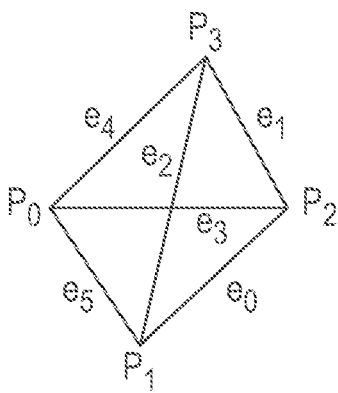
Figure 4:
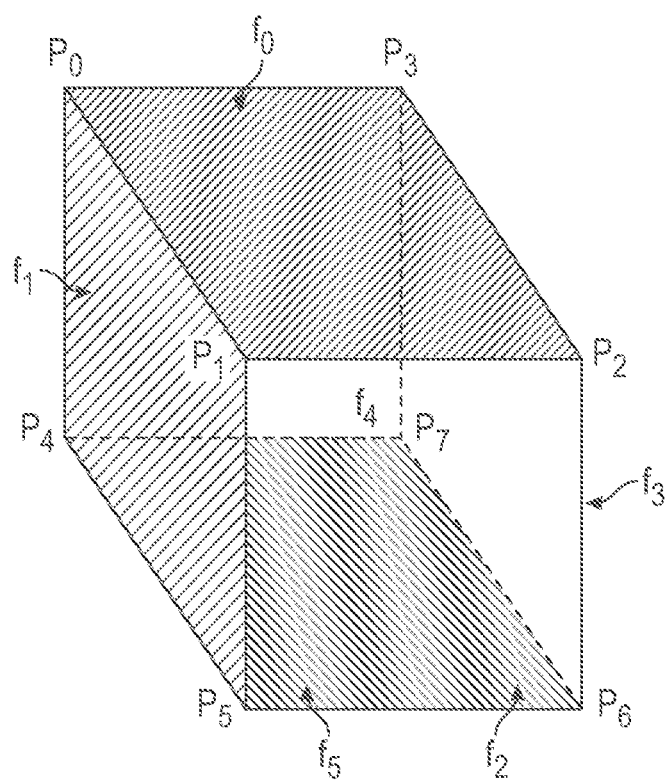
FIG. 4 is an illustrative perspective view of an illustrative example primitive hexahedral cell.

FIG. 3A-3C are illustrative perspective views of an example primitive tetrahedral volumetric cell that may be included within a volume mesh in a unified mesh format that contains both surface vertices and internal vertices. The tetrahedral cell includes four vertices P0-P3, six edges e0-e5, and includes four faces F0-F3. One of the four faces F0-F3 may be included as a portion of a surface portion of the volume mesh while the remaining three faces are internal to the volume mesh, for example. It will be appreciated that if one of the faces of the example tetrahedral cell forms a portion of the surface mesh, then each of the three vertices of that surface face shares a separate edge with the one remaining other non-surface vertex, which is disposed internal to the volume mesh. FIG. 4 is an illustrative perspective view of an illustrative example primitive hexahedral cell that may be included within a volume mesh in a unified mesh format that contains both surface vertices and internal vertices. One of the six faces F0-F5 may be included as a portion of the surface mesh while the remaining five faces are internal to the volume mesh, for example. The hexahedral cell includes eight vertices P0-P7, twelve edges, and includes six faces F0-F5.

Figure 5:
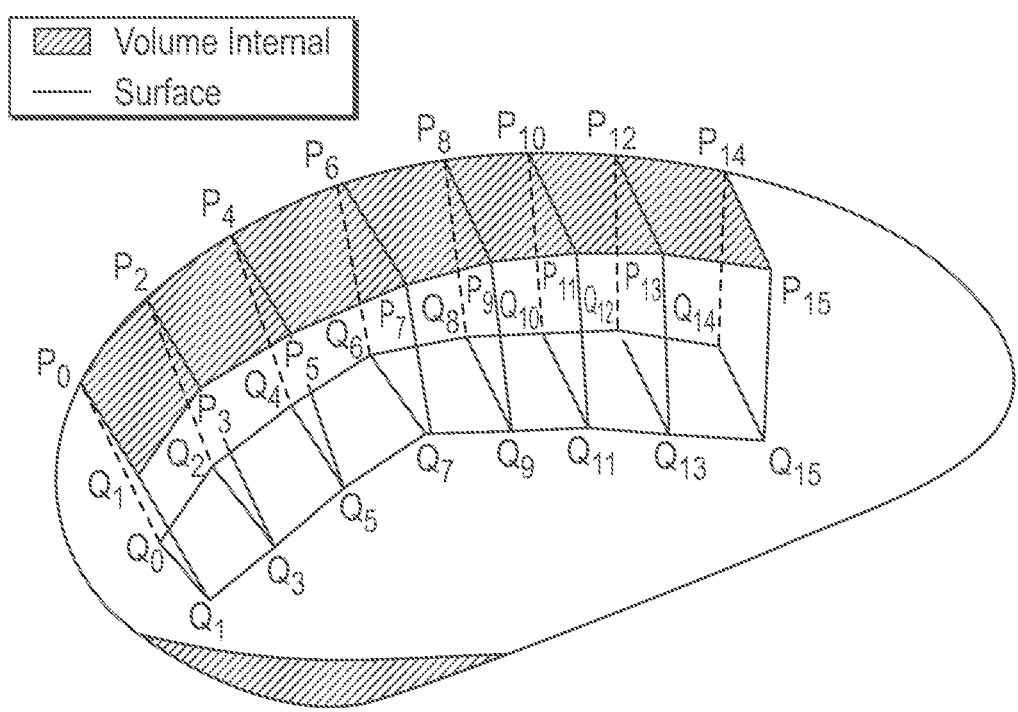
FIG. 5 is an illustrative perspective view of an example volume mesh representation of a physical tissue object that includes a plurality of volumetric hexahedral cells.

FIG. 5 is an illustrative perspective view of an example volume mesh representation of a physical tissue object that includes a plurality of volumetric hexahedral cells. Only a few example hexahedral cells are shown so as to not overcomplicate the drawings and explanation. Each of the example cell shown in FIG. 5 has one face that acts as a surface mesh portion of the volume mesh. Each volumetric hexahedral cell has eight vertex nodes that are associated with edges to define six faces. For example, a first volumetric hexahedral cell includes vertex vertices (P0, P1, P2, P3, Q0, Q1, Q2, Q3) that define an integral portion of the volume mesh. Vertices (P0, P1, P2, P3), which are a subset of the vertex nodes within first hexahedral cell define a face that forms an integral surface mesh portion of the volume mesh. Internal vertex pairs (P0, Q0), (P1, Q1), (P2, Q2) and (P3, Q3) each defines an internal edge. Thus, the first volumetric hexahedral cell includes both surface vertices and internal vertices. Similarly, for example, a second volumetric hexahedral cell includes vertex vertices (P2, P3, P4, P5, Q2, Q3, Q4, Q5). The second volumetric hexahedral cell includes surface vertices (P2, P3, P4, P5) that define a face that forms an integral surface mesh portion of the volume mesh. Internal vertex pairs (P2, Q2), (P3, Q3), (P4, Q4) and (P5, Q5) each defines an internal edge. Thus, a volume mesh includes primitive volumetric cells that have both surface vertices that define a surface portion of the volume mesh and internal vertices that define an internal portion of the volume mesh.

FIG. 6 is an illustrative drawing representing certain details of a unified mesh format (UMF) representation of the volume mesh of FIG. 5. The unified mesh information structure includes a combined nodes list which contains a first ordered list of surface vertices and a separate second ordered list of internal vertices. In some embodiments, a single list is provided for all nodes, which is sliced into sub-lists: a surface node sub-list and an internal nodes sub-list. To access these lists separately the system provides a base address to the combined list and the count of surface nodes as well as all nodes in the list. An advantage of list with sub-list data structure is that after computing the deformation-related displacements of vertices due to virtual external forces, position/displacement information for all nodes (surface or internal) may be updated. Having all nodes under one overall list improves performance in updating positions/displacements. However only surface nodes need be accessed during shading to apply color or texture to a surface. Co-locating the surface nodes together in a sub-list provides improves access to the surface nodes during shading since they are not comingled with the internal nodes, for example. Co-locating the surface nodes together in a sub-list that precedes a sub-list of internal nodes improves fast access to these nodes since they are at the top of the list, for example.

More specifically, the list of surface vertices and the list of internal vertices are ordered with the surface vertices disposed first, preceding the internal vertices. The surface vertices are accessed more frequently due to the shading procedure. The same base address can be used in simulation and rendering and there is no need to compute effective addresses when in rendering procedure. This organization of list and sub-lists is advantageous since, after computing the displacements due to external forces, all nodes (surface or internal) may require updating. Having all nodes under a single list improves the performance since a simulation is typically runs on it device memory and it is more efficient to perform one memory transaction instead of two per cycle. When applying color or texture to the surface, for example, the system directly accesses the surface nodes only, which is already available at the base address. Moreover, in some embodiments, since the frequency of access to the surface nodes generally is higher than that of the internal nodes due to shading computations, it may be more efficient to supply the base address to the list and the number of surface nodes so that the same base address is valid for both simulation and rendering procedures. Alternatively, if internal nodes are placed first in the list then the pointer to the beginning of the surface nodes list is different and should be computed and supplied separately for the rendering procedure.

As explained above, each vertex in the unified mesh format representation of the volume mesh has a three-dimensional location. For example, assume that vertex P0 has location ($X_{P0}$, $Y_{P0}$, $Z_{P0}$) and vertex Q0 has location ($X_{Q0}$, $Y_{Q0}$, $Z_{Q0}$). Surface vertices P0-P15 are associated with shading parameters, e.g., color ($C_n$), normal ($n_n$), that are used by the shading engine. All vertices, surface and internal, are associated with viscoelasticity parameters, e.g., mass ($M_n$), Young's modulus ($\gamma_n$) and Poisson Ratio ($\sigma_n$), which are used by the simulation engine.

Figure 7:
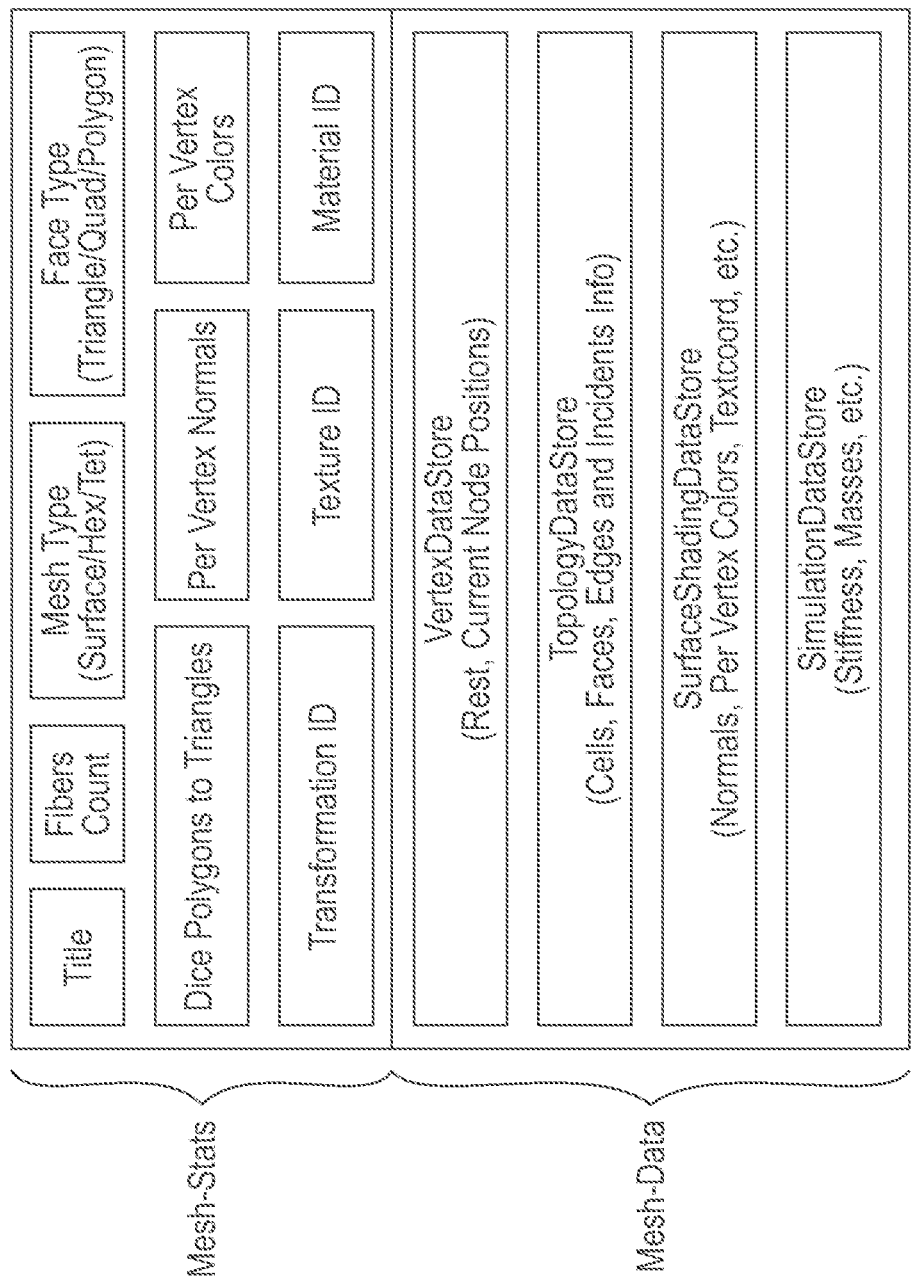
FIG. 7 is an illustrative drawing showing a volume mesh data structure to represent a volume mesh in accordance with some embodiments.

FIG. 7 is an illustrative drawing representing a volume mesh data structure stored in a storage memory device to represent a volume mesh in accordance with some embodiments. By way of overview, during simulation, the mass and stiffness properties associated per each vertex are loaded into a simulation engine from a SimulationDataStore. The TopologyDataStore is accessed to extract connectivity information between nodes using edges and the cellular elements (e.g. tetrahedra, hexahedra). Displacements and updates of the current node positions are accessed in the VertexDataStore. By way of further overview, during shading, a shading engine is loaded with per vertex color and normal attributes from a SurfaceShadingDataStore and with current vertex positions from the VertexDataStore. Surface portions of the mesh are shaded using this information on a graphics processing unit (GPU) component of the shading engine to produce shader output values in a frame buffer is sent for rendering.

More particularly, still referring to FIG. 7, in accordance with some embodiments, a fiber in the system is defined as a memory-aligned dynamic array that provides storage for specific mesh attributes e.g. position, normal, color etc. The SurfaceShadingDataStore portion of the volume mesh data structure includes surface shading data such texture coordinates, normal and colors are stored for rendering purposes. The TopologyDataStore portion of the volume mesh data structure includes connectivity information such as edges, faces, and volumetric cells in associated lists of edges, faces, and cells in that order. A VertexDataStore portion of the volume mesh data structure includes current and at-rest three-dimensional locations of all surface vertices and for all internal vertices. A collection of fibers create a structure of arrays that define a specific property of the mesh, e.g. all shading information are defined in the SurfaceShadingDataStore and all mesh connectivity information are stored in the TopologyDataStore. This grouping approach provides a clear definition of the roles per each data store. A mesh-stats portion of the data structure provides additional information about the current mesh, i.e. name and total number of fibers that defines the current mesh, the type of volumetric cells and surface faces used and other associated information such as external transformations, textures and materials for the current mesh. During a simulation time-step the current and rest positions of all nodes are loaded from the VertexDataStore to the simulation engine, other physically-based attributes associated per each vertex are fetched from the SimulationDataStore, such as masses and stiffness properties that define the internal volumetric properties of the mesh. The TopologyDataStore provides the configuration of each volumetric cell e.g. tetrahedral elements and the associated connectivity links between nodes from the edges. Using this information the system computes the internal stress and strains of the volume due to virtual internal and external forces and solves for displacements. The current positions of all nodes may be updated based upon the computed displacements. When the simulation time-step is completed, updated vertex positions and per vertex color and normal properties are supplied from the SurfaceShadingDataStore to the rendering system for shading. Using existing techniques such as Phong shading model, a final color associated per each pixel is determined based upon the configuration of light sources in the scene and the supplied surface properties. See, Shirley, P., Marschner, S., et al. (2009). *Fundamentals of computer graphics*. AK Peters, Ltd., at page 236 for a discussion of the Phong shading model.

Figure 8A:
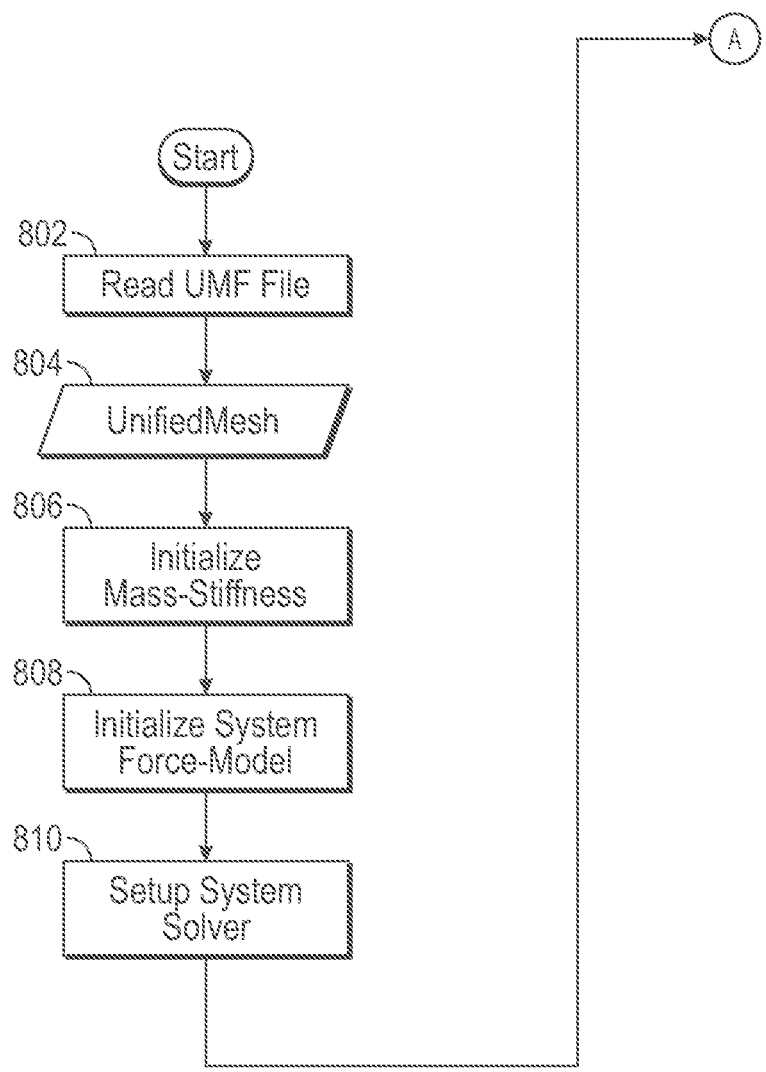
FIG. 8A is an illustrative flow diagram representing set up of a computing system to use a UMF volume mesh in simulation and shading in accordance with some embodiments.
Figure 8B:
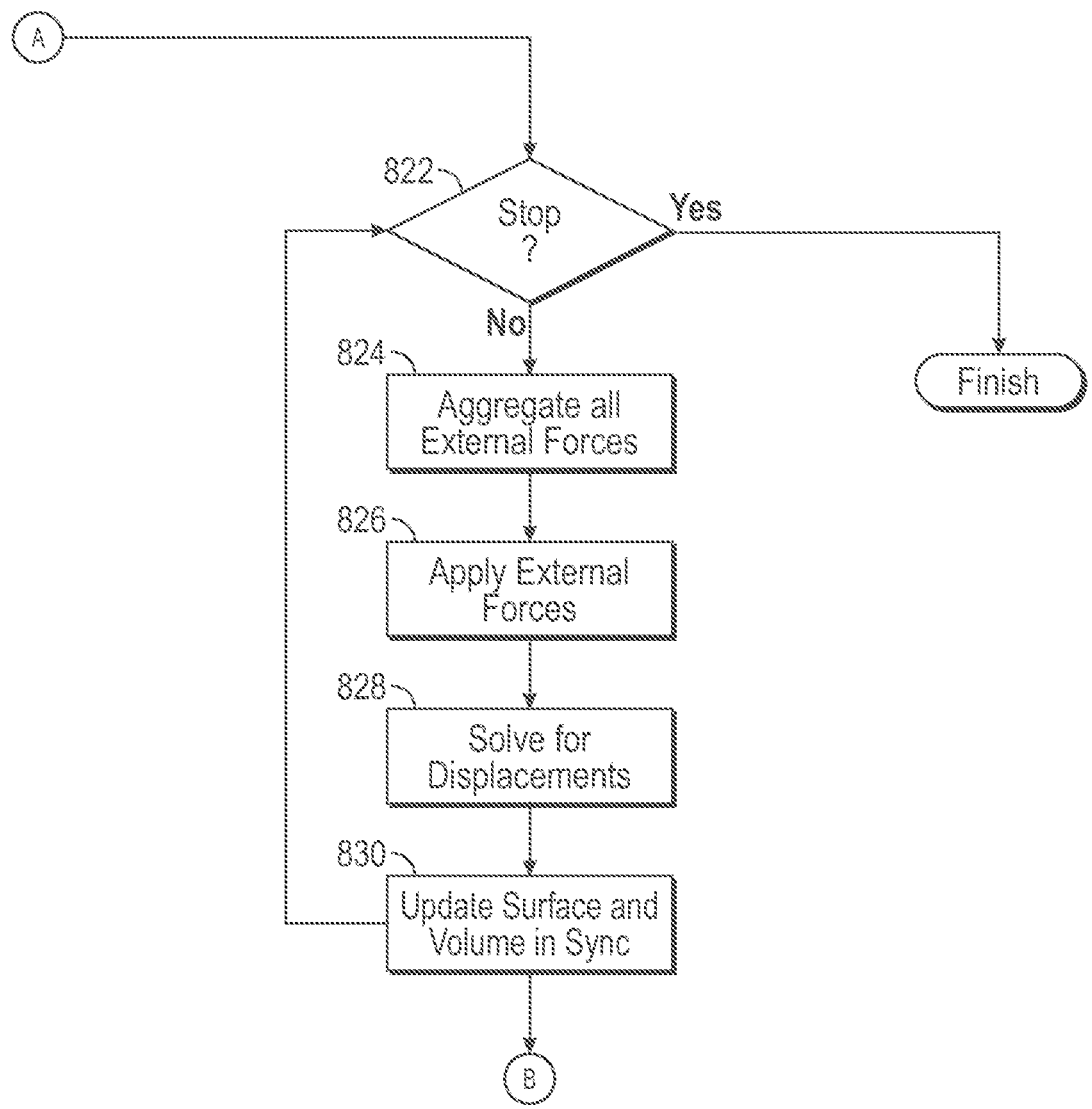
FIG. 8B is an illustrative flow diagram representing a simulation process based upon a UMF volume mesh in accordance with some embodiments.
Figure 8C:
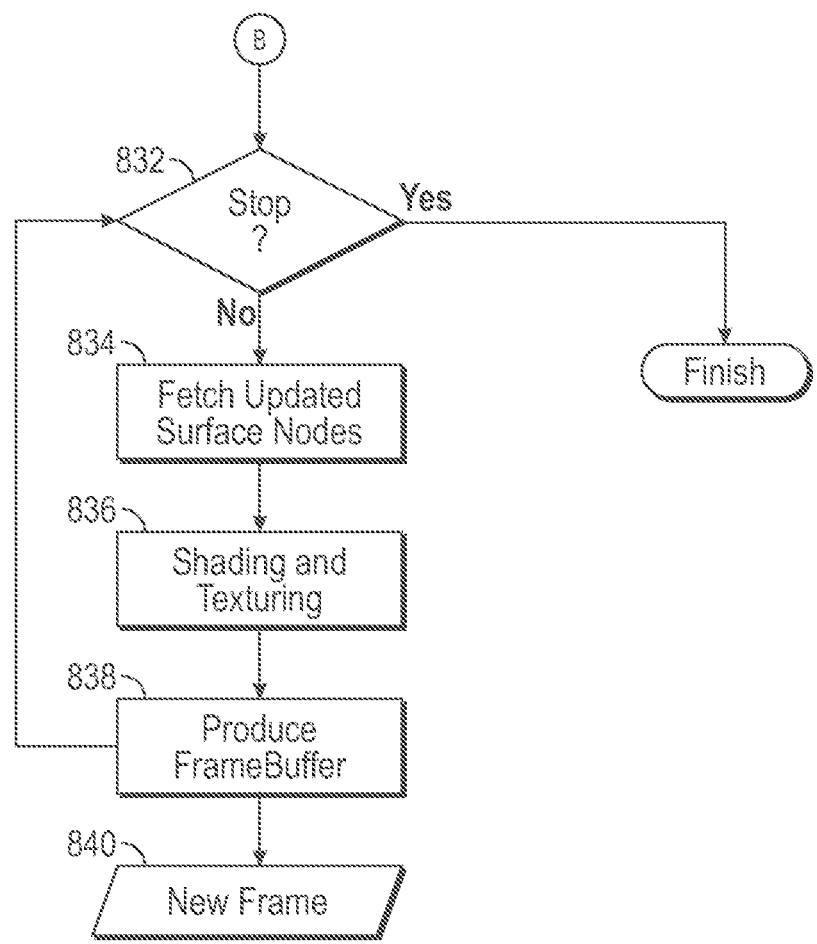
FIG. 8C is an illustrative flow diagram representing a shading process based upon a UMF volume mesh in accordance with some embodiments.
Figure 9A:
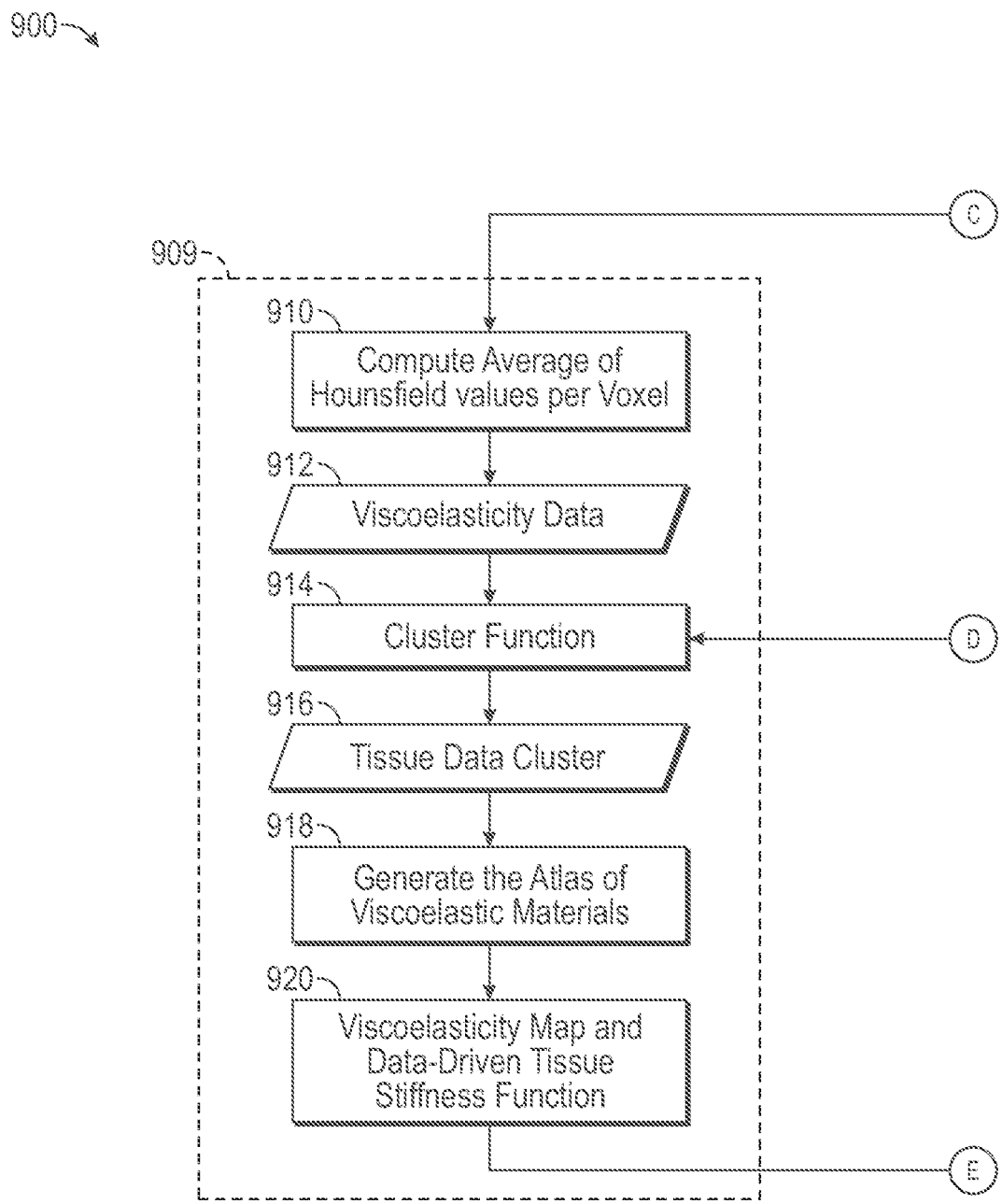
FIGS. 9A-9D is an illustrative flow diagram representing a process performed by simulation and shader system of FIG. 1, in accordance with some embodiments.
Figure 9B:
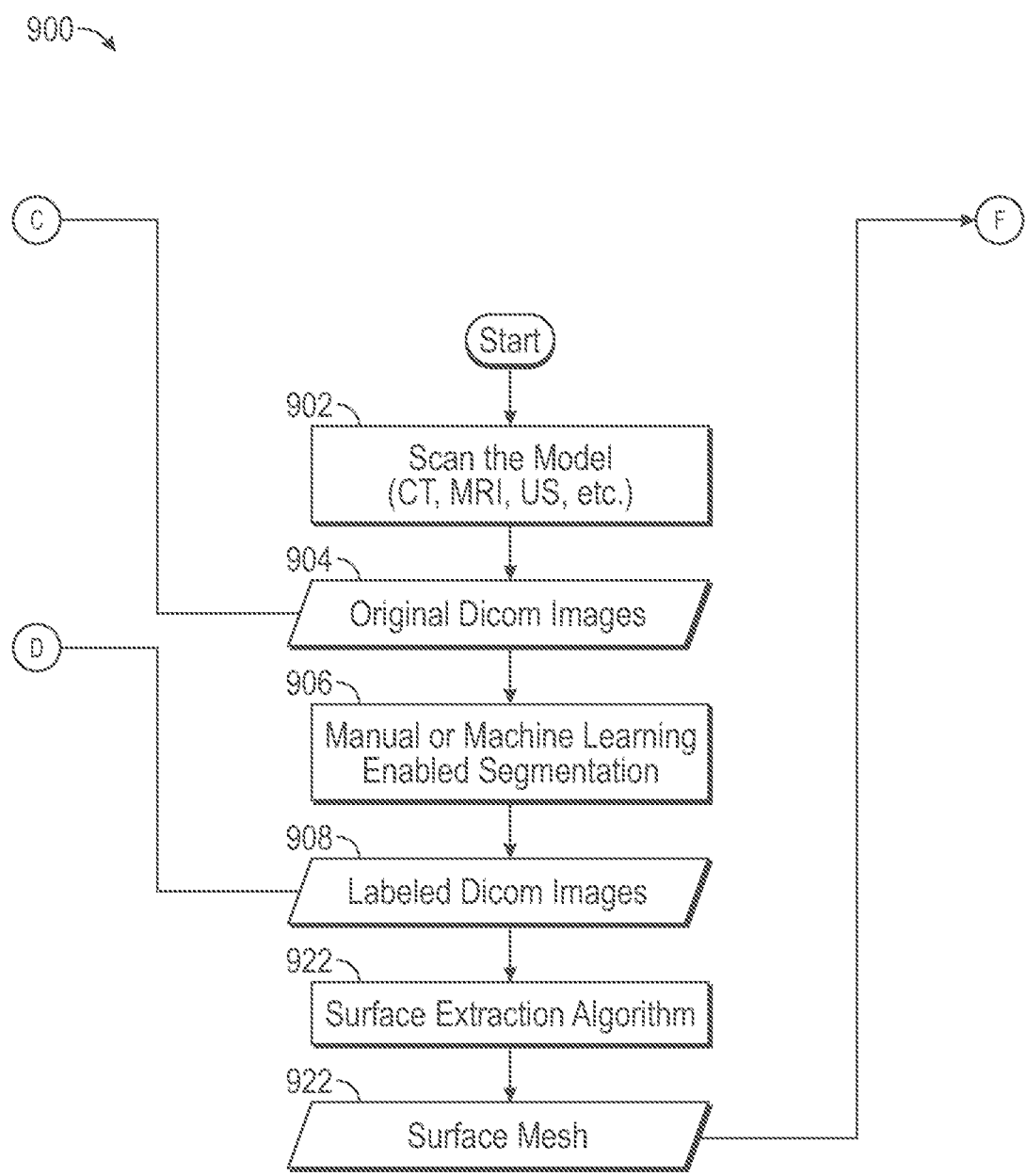
Figure 9C:
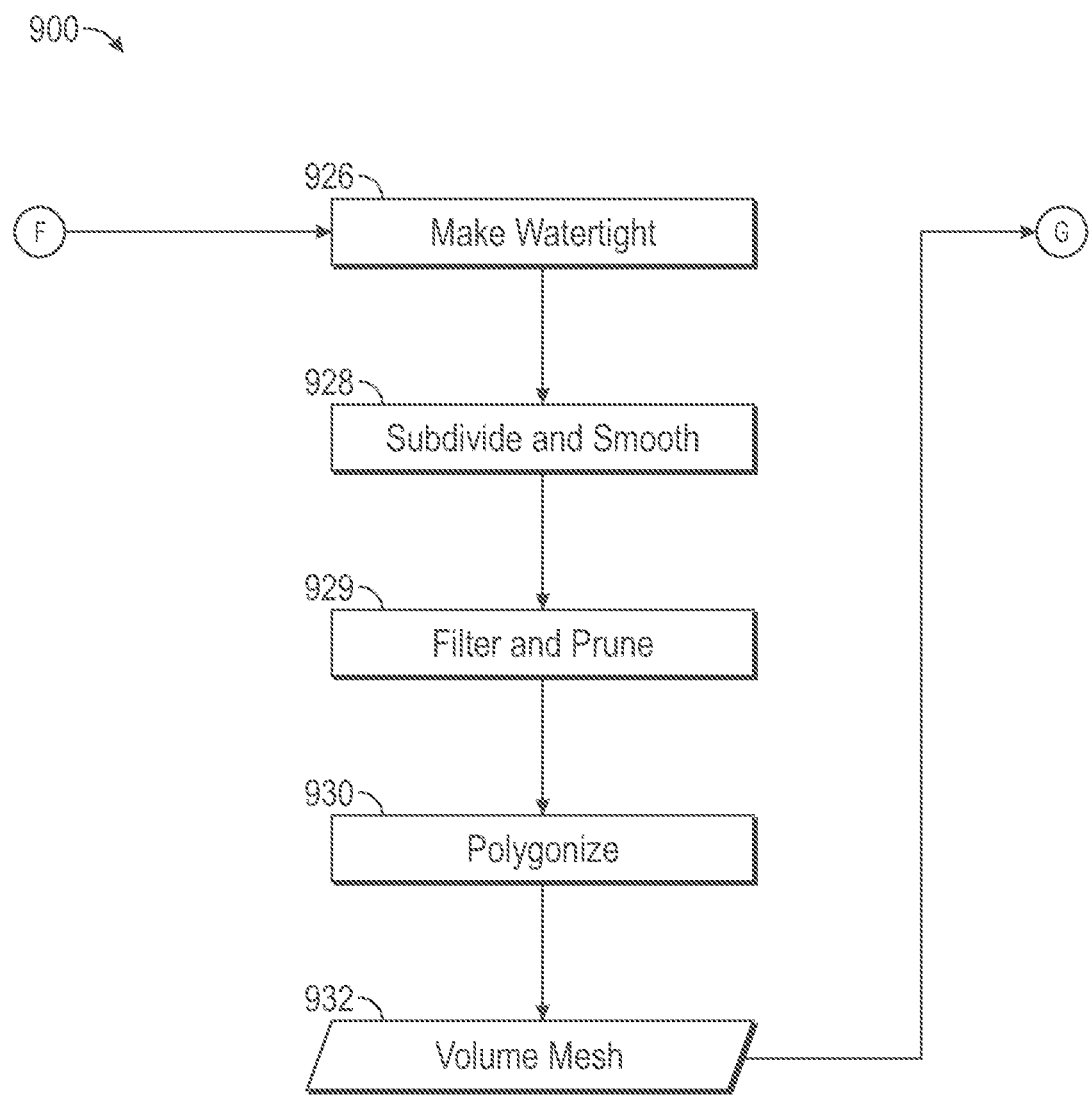
Figure 9D:
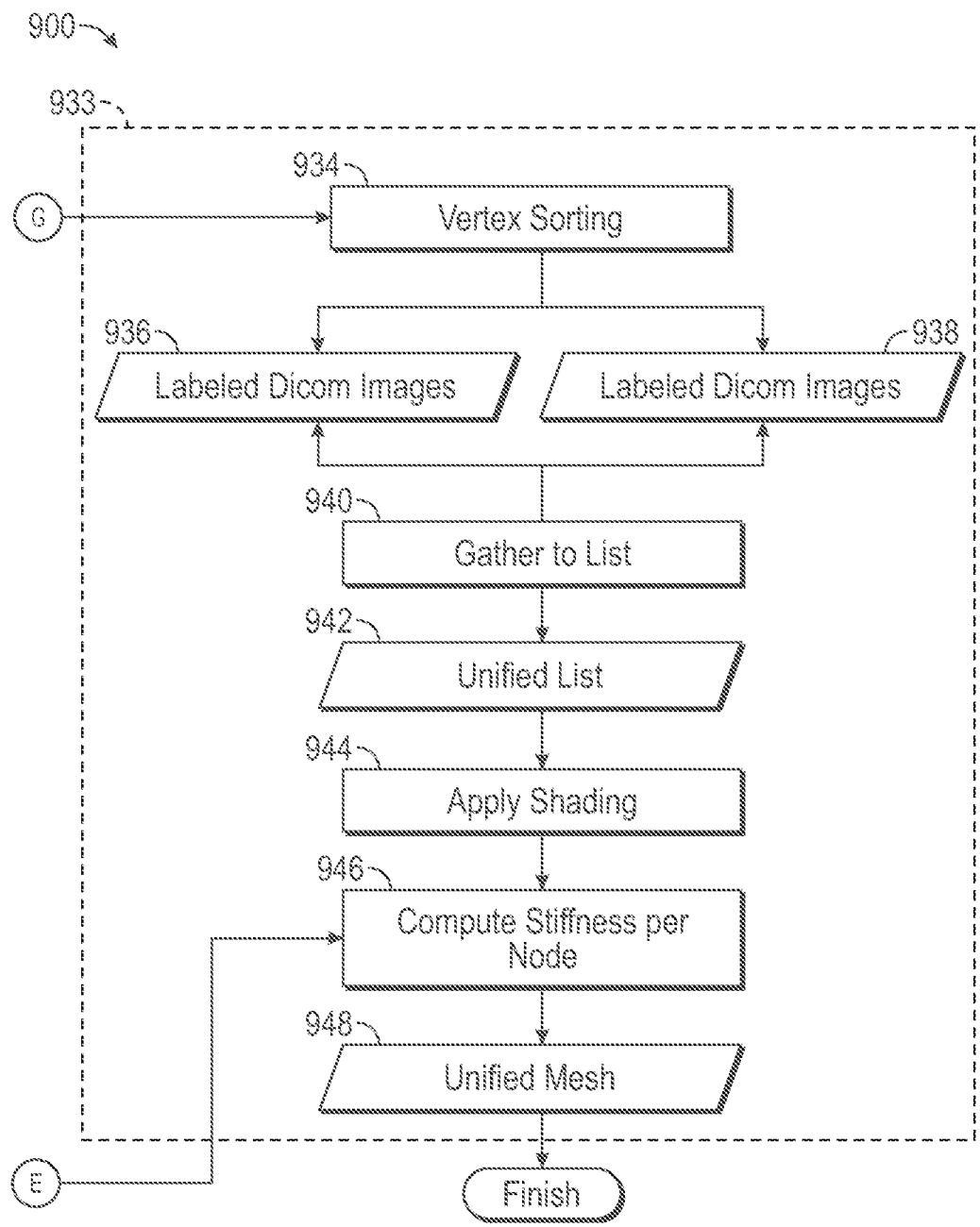

FIGS. 8A-8C are illustrative flow diagrams representing processes to use a volume mesh in a unified mesh format (UMF) during simulation and shading in accordance with some embodiments. Functional blocks of the processes configure one or more computing systems to perform algorithmic processes corresponding to the functions. FIG. 8A is an illustrative flow diagram representing a set up process 800 to set up a computing system to act as a simulation engine 106 and to act as a shader engine 110 to use a UMF volume mesh in simulation and shading. Functional block 802 reads a UMF file 804 into a storage memory. Functional block 806 initializes mass-stiffness matrices, which involves setting the matrices and filling them with the data stored in a file. Functional block 808 initializes a system force model. Functional block 810 sets up a system solver.

FIG. 8B is an illustrative flow diagram representing a simulation process 820 based upon a UMF volume mesh in accordance with some embodiments. A computing system configured to act as the simulation engine 106 performs the simulation process 820. Functional decision block 822 determines whether to continue with simulation. Assuming yes, functional block 824 aggregates all external forces upon the UMF volume mesh. Functional block 826 applies the external forces to the UMF volume mesh. Functional block 828 solves for three-dimensional displacements of vertices within the UMF volume mesh. Functional block 830 updates the surface vertices and updates the internal vertices within the UMF volume mesh based upon displacements determined by the solver based upon finite element analysis procedures. See, Finite Element Procedures, by Klaus-Jurgen Bathe, PHI Learning Private Limited, New Delhi (1996). Control flows to back functional decision block 822, which again determines whether to continue with simulation. It will be appreciated that the simulation cycle that includes functional blocks 822-830 represents application of one time increment of aggregated force upon the UMF volume mesh.

FIG. 8C is an illustrative flow diagram representing a image rendering process 830 based upon a UMF volume mesh in accordance with some embodiments. A computing system configured to act as the shader engine 110 performs the image rendering process 830. Functional decision block 832 determines whether to continue with shading. Functional block 834 fetches updated surface vertex information from the UMF volume mesh. Functional block 836 applies shading and texturing based upon fetched vertex locations, colors and normals. Functional block 838 produces a frame buffer based upon the shading and texturing information to produce a new frame 840 for use to generate an image of the simulated deformation of the volume mesh on a computer display screen. Control flows back to functional decision block block 834 determine whether to produces the next frame in the rendering process.

FIGS. 9A-9D is an illustrative flow diagram representing a process 900 performed by simulation and shader system 100 of FIG. 1, in accordance with some embodiments. The simulation and shader system 100 is configured to act as a data storage and retrieval system to configure a computer memory storage device, according to a unified mesh format (UMF) representation 120 of a volume mesh 118, to represent a physical anatomical tissue object 114. Functional blocks of the process represent configuration of the system 100 to perform algorithmic processes to create, a UMF volume mesh 120 for use with a computing system configured to act as the simulation engine 106 performs the simulation process 820. by the simulation engine 106 and the shading engine 110.

A scanning device (e.g., CT, MRI or Ultrasound) 902 scans an anatomical tissue object to produce an image scan data set. A scanned image data set within data storage memory block 904 represents an image scan data set received from the scanning system that may be stored in a computer readable storage device. The received image scan data includes three-dimensional, i.e. (x, y, z) location based, tissue data that may include image data used by a display system to display a visual image representation of the tissue structure, such as a CT, MRI or Ultrasound image, on a display device, for example. In some embodiments, the three-dimensional tissue data set may be organized according the Digital Imaging and Communications in Medicine (DICOM) image format, which is a standard format for medical images. The tissue data set may include individual pixel values corresponding to individual three-dimensional locations within a tissue structure. Cross-sectional slices through the three-dimensional data set may be used to display cross-sectional image slices of the three-dimensional tissue structure. The image scan data set may include image data such as gray scale information or color information, for example, that is indicative of tissue constituency such as tissue density. Tissue density is indicative of tissue type. Specifically, different gray or color scale values at different three-dimensional locations may indicate different tissue densities or types at those different locations.

A segmenter functional block 906 configures a computer system to perform a segmenting process to segment the received image scan data set according to different tissue types represented in the image scan data set. A labeled data set data within memory storage block 908 indicates that the segmenting functional block 906 produces a labeled image data set that includes label information applied to the original received image data set that may segment the image data set based upon tissue type. The segmenter functional block 906 may be operative manually, through machine learning techniques, or through a combination of the two. The received image data set may include grey scale values arranged in patterns that correspond to the tissue structures that they represent. For example, blood vessels and bone tissue structures may have different corresponding gray scale image values and different corresponding three-dimensional shape patterns. A computer system (not shown) used by a segmenter (human operator and/or machine) uses the image data set to display image slices of anatomical object, and the segmenter uses knowledge of anatomy to segment tissue images according to tissue type. More particularly, the segmenter may provide input to a computer user interface to add label information to different portions of the image data set within the labeled data set of memory storage block 908 to distinguish different tissue types that may be represented in the image data set so as to segment the image data set according to tissue type. More specifically, the segmenter functional block 906 associates label information with three-dimensional locations within the labeled data set of memory storage block 908 so as to segment portions of the image data set that are associated with different tissue types. A segmenter may use a combination of gray scale values and shape patterns as a basis to segment tissue data according to tissue type such as tissue data corresponding to blood vessels and tissue data corresponding to bone, for example.

A first process flow segment indicated by dashed lines 909, which encompasses functional blocks 910-920, produces a viscoelasticity map based upon three-dimensional (3D) image scan data model 116, in accordance with some embodiments. A voxel viscoelasticity determination functional block 910 configures the computer system to compute viscoelasticity values for the image scan data set. In some embodiments, the three-dimensional tissue data set may be organized as a voxel grid. More particularly in accordance with the DICOM image format, the image data may include an axis-aligned voxel grid of data samples. Each vertex in the voxel grid is associated with a pixel value. Moreover, in some embodiments, the viscoelasticity values are represented as Hounsfeld unit (HU) values. Each individual pixel value within the three-dimensional tissue data set may have a gray scale value within a numerical range of one to two-hundred fifty-six, for example, that is indicative of the attenuation of X-rays by tissue at the corresponding tissue location, which can be expressed in terms of HUs. Thus, in some embodiments, a voxel is represented as eight pixel values, one pixel value at each of eight vertices. The voxel viscoelasticity determination functional block 910 configures the computer system to determine an HU value corresponding to an entire voxel based upon HU values of the pixels at the voxel's vertices. More specifically, an HU value corresponding to an entire voxel may be determined through linear interpolation such as based upon an average of the HU values of the pixels at the voxel's eight vertices. Thus, in some embodiments a three-dimensional location at a center of a voxel within the image scan data set is assigned an HU value computed as an average of the HU values associated with the vertices of the voxel. Voxel viscoelasticity data of memory storage block 912 includes a viscoelasticity data set structure that may be stored in a computer readable storage device. Thus, the viscoelasticity data set structure may include individual viscoelasticity values, determined using the functional block 910, that correspond to and that are associated, within the viscoelasticity data set structure, with three-dimensional locations that correspond to individual voxel centers.

A cluster functional block 914 configures the computer system to cluster voxel HU value data according to tissue type. Cluster functional block 914 superimposes the labeled data set of memory storage block 908 with the voxel viscoelasticity data of memory storage block 912 to produce a tissue cluster data within memory storage block 916 in which tissue viscoelasticity values are clustered based upon tissue type. For example, if the anatomical object is a kidney and the segmenter functional block 906 segments the kidney into four tissue segments (e.g., parenchyma, collecting system, arteries and veins), then the tissue cluster data within memory storage block 916 includes viscoelasticity values (e.g., per voxel HU values) that are clustered based upon the tissue type that they belong to. Thus, the cluster functional block 914 associates three-dimensional locations corresponding to viscoelasticity values in the voxel viscoelasticity data block with three-dimensional locations in the labeled data set of memory storage block 908 so as to superimpose the two data sets to indicate boundaries between viscoelasticity values belonging to different tissue types. The tissue cluster data within memory storage block 916 also may indicate points of attachment between tissues. For example, in some embodiments, the tissue cluster data within memory storage block 916 may indicate the number of voxels disposed between adjacent tissue types and the shortest path between adjacent tissue types. The cluster data indicates anchor points, linkages and paths between different tissue types, which may be used during simulation to indicate transference of forces between adjacent tissues, for example. In some embodiments, the cluster functional block 914 produces tissue cluster data organized in a tree data structure that indicates parent and child relationships between different tissue structures, for example.

A mapping functional block 918 configures the computer system to produce a three-dimensional viscoelasticity map within memory storage block 920 for a tissue type, based upon tissue cluster data within memory storage block 916. The mapping functional block 918 configures the computer system to map the tissue viscoelasticity values determined by voxel viscoelasticity determination functional block 910 to three-dimensional locations corresponding to a tissue structure type identified by the cluster functional block 914. A separate viscoelasticity map may be created for each identified tissue type. The viscoelasticity map within memory storage block 920 includes a data structure that associates viscoelasticity values (e.g., HU values) with three-dimensional locations within the image data set.

The viscoelasticity map of memory storage block 920 may act as a tissue viscoelasticity look-up-table (LUT) data structure that indicates tissue viscoelasticity based upon three-dimensional location. The viscoelasticity map acting as a LUT allows for ease or real-time determination of viscoelasticity at different tissue locations. For example, the map may indicate that a tissue portion at a three-dimensional location at a tissue surface has a certain viscoelasticity value, and the map may indicate that a tissue portion at a three-dimensional location tissue location nearer to a tissue core has a different viscoelasticity.

A surface extraction functional block 922 configures the computer system to produce a surface mesh structure to store in memory storage block 924, based upon the labeled image data set of memory storage block 908. In some embodiments, a different surface mesh structure is determined for each different tissue type labeled by the segmenter functional block 906. A space partitioning technique such as "marching cubes" may be used to determine voxels within the labeled image data set having faces associated with tissue surfaces. Fundamentals of Computer Graphics, Third Edition, by M. Ashikhmin et al., A. K. Peters, Ltd. (2009) at pages 709-717 describes techniques to determine isosurfaces within an image data set.

Several post-processing steps further refine the surface structures within the memory storage block 924 to prepare it for use in producing a volume mesh 932. A watertighting functional block 926 performs a watertighting process to search for holes in a surface mesh structure within the memory storage block and to patches them to create a solid surface mesh structure. A watertight mesh is one in which all of the surfaces are complete, the lines of the mesh create valid elements suitable for use in simulation, and the mesh properly connects to adjacent surfaces around the surface mesh perimeter so that the volume is fully enclosed. A need for a watertighting during post-processing may arise, for example, because the original image scan data set within memory storage block 904 may be missing data for certain portions of tissue structure object or be cut off due to scanning device boundaries or mispositioning of the tissue structure object relative to the scanning system. The watertighting process may generate triangular or quadrilateral patch structures to fill holes based upon extrapolation from the existing surface structure within the memory storage block 924.

A smoothing functional block 928 performs a smoothing process to remove artifacts from a surface mesh and to replace them with a smoother more continuous surface pattern. A need for a smoothing during post-processing may arise, for example, because portions of the original image data set within memory storage 904 may be blocky or pixilated due to inaccurate or incomplete scan data. As a consequence, the segmenter functional block 906 may produce labels that do not accurately represent transitions between different tissue structures. For example, a DICOM image may not have been clear in some area and so the segmenter may simplify and label to indicate an abrupt change from one tissue structure to the next. Because of such inaccurate labeling, the surface extraction functional block 922, in turn, may produce a surface mesh structure that includes artifacts such as a staircase effect in some portions of surface mesh structure, for example. The smoothing functional block 928 removes these artifacts from the surface mesh structures.

Pruning functional block 929 performs a filter and prune process to reduce the number of vertices in the surface mesh. The filter and prune process may remove overhanging edges such as overhanging edges of a primitive tringle or quadrilateral, for example. The filter and prune process also may reduce the number of primitive structures used to represent a portion of a mesh surface. For example, it may be possible that a large smooth portion of the surface mesh can be represented using a smaller number of larger triangles. Fewer triangles (primitives) means fewer vertices which reduces latency during simulation. Thus, the filter and prune process may reduce the number of triangles used to represent smooth portions of a surface mesh. Functional block 930 performs a tetrahedralization process to produce one or more volume mesh structures 932 using primitive volumetric cells based upon the post-processed surface mesh structure 924.

A polygonization functional block 930 generates internal primitive volumetric cells that collectively create the volume mesh structure within memory storage block 932, which is encompassed by the surface mesh within memory storage block 924. In some embodiments, the primitive volumetric cells include tetrahedral cells. In some embodiments, the primitive volumetric cells include hexahedral cells. The polygonization functional block 930 may employ known polygonization methods such as Delaunay triangulations to generate the volume mesh structures 932. A description of polygonization is provided in Delaunay Mesh Generation by Siu-Wing Cheng, et al., CRC Press (2012), at pages _-_. The primitive volumetric polygonal cells are used during simulation involving a finite element analysis process to simulate deformation of tissue structure in response to forces applied to the tissue. Each primitive volumetric polygonal structure is associated with multiple vertex nodes and each vertex node is associated with a three-dimensional volume location. A separate volume mesh structure may be produced for each separately labeled tissue type. For example, as mentioned above, kidney includes at least four different tissue types, artery, vein, parenchyma and collecting system. Thus, the segmenter functional block 906, labels original scan data within memory storage block 904 that represents a kidney with at least four different labels, each corresponding to a different tissue type. In that case, the polygonization functional block 930 produces four separate volume mesh structures that correspond to the four differently labeled portions of the original data set 904.

A second process flow segment indicated by dashed lines 933, which encompasses functional blocks 934-948, produces the unified mesh format representation 120 of the volume mesh 118, in accordance with some embodiments. Sorting functional block 934 sorts vertices of primitive volumetric cells within a volume mesh structure into a corresponding first list of surface vertices within memory storage block 936 and a corresponding second list of internal vertices within memory storage block 938, which may be stored in a computer readable storage device. The sorting functional block 934 implements a sorting process that performs a top-down traversal of the primitive volumetric cells. By way of overview, in a top-down traversal we start from a volumetric cell and then proceed to the faces associated with that cell (6 faces for hexahedra and 4 for tetrahedral) and then per each face, the edges associated with that faces are visited. In the end each edge is associated with two end points i.e. nodes. Alternatively, by way of overview, in a bottom-up traversal we start from a node and then visit all adjacent edges to that node. And then per each edge, all adjacent faces to that edges and lastly per each face all adjacent cells to a given face are visited.

More specifically, a sorting process in accordance with some embodiments identifies faces of each primitive volumetric cell. For each identified cell face, sorting process identifies the edges of the cell. Each volumetric cell edge has two endpoint vertices. The sorting process determines for each identified cell face, whether the identified face is associated with more than one volumetric cell. In response to a determination that an identified face is associated with only one volumetric cell, the sorting process determines that the vertex nodes at the endpoints of the edges of the identified face are surface vertex nodes, and the sorting process enters identifiers for these surface vertex nodes in the first list structure, which includes surface vertices stored in the memory storage block 936. In response to the sorting process determining that an identified face is associated with more than one volumetric cell, the sorting process determines that the vertex nodes at the endpoints of the edges of the identified face are internal vertex nodes, and the sorting process enters identifiers for these internal vertex nodes in the second list structure, which includes internal vertices stored in the memory storage block 938.

Merge functional block 940 merges the first, surface, list within memory storage block 936 and the second, internal, list within memory storage block 938 that represent a volume mesh structure corresponding to a tissue type to produce a merged (unified) list structure within memory storage block 942. In some embodiments, the unified list structure within memory storage block 942 orders the surface vertices in the unified list precede the internal vertices in the unified list. It will be appreciated that surface nodes are accessed more frequently than the internal nodes since surface nodes are passed through both shading and simulation. If the internal nodes are placed first then the pointer to the beginning of the surface nodes list should be computed and supplied separately for the rendering procedure. In case of cutting the volume, new faces and cells may be produced and appended to the list. Then the base address to the surface nodes may be recomputed each time.

Moreover, it will be understood that although the surface and internal vertices are stored separately in first and second lists within the storage memory block 942, they are constituents of the volume mesh produced by the polygonization functional block 930, and that during simulation, virtual forces may be applied to these vertices to cause deformation of the volume mesh to simulate deformation of the physical anatomy object represented by the volume mesh in response to real physical forces.

Shading functional block 944 associates color and texture parameter values to surface vertex nodes for use in a shading process performed in the course of a simulation. Shading produces may be employed to produce a more realistic image of a tissue structure based upon its angle to incident light and its distance from incident light. Shading involves altering the appearance of a three-object, based upon its color and texture and its angle with respect to incident light and its distance from the incident light. Shading involving color and texture is described in Fundamentals of Computer Graphics, Supra., at pages 69-89 and at pages 177-180.

A vertex viscoelasticity determination functional block 946 determines viscoelasticity values for surface and internal vertices within the unified list within memory storage block 942. More specifically, each node of the unified list in block 942 is associated with a three-dimensional (x, y, z) location. For each three-dimensional location of a vertex node in the unified list 942, the functional block 946 determines a corresponding viscoelasticity value based upon the map in memory storage block 920.

The vertex viscoelasticity determination functional block 946 configures the computer system to use the viscoelasticity map of memory storage block 920 as a LUT to determine tissue viscoelasticity values to associate with three-dimensional locations of vertices within a volume mesh representation of a tissue object based upon viscoelasticity values at corresponding three-dimensional locations within a scanned image data set obtained for the tissue object. The functional block 946 implements a data driven viscoelasticity determination function in which a three-dimensional (x, y, z) tissue location is received as an input value and a scalar value representing tissue viscoelasticity at the received location is provided as an output value. The scalar value may include a Young's modulus in terms of stiffness, for example. The vertex viscoelasticity determination functional block 946 accesses the viscoelasticity map of memory storage block 920, which acts as a LUT, to produce a three-dimensional tissue location based viscoelasticity value in response to a received three-dimensional input location.

In some embodiments, the vertex viscoelasticity determination functional block 946 determines a viscoelasticity value to associate with a three-dimensional location input location by interpolating between average voxel values associated with three-dimensional locations nearby to the received three-dimensional input location. More particularly, in some embodiments, functional block 946 interpolates a viscoelasticity value to return in response to a received three-dimensional input location based upon viscoelasticity values associated with a prescribed number of viscoelasticity values associated with three-dimensional locations closest to the received three-dimensional input location.

Thus, for each surface vertex and for each internal vertex within the unified list, the functional block 946 uses a three-dimensional location associated with the vertex in the volume mesh as an input location. The functional block determines a corresponding value within the viscoelasticity map of memory storage block 920. Determining the corresponding value may involve interpolation between multiple viscoelasticity values associated with three-dimensional locations in the viscoelasticity map that are nearby to the input location. For each surface vertex and for each internal vertex, the functional block 946 stores a corresponding determined viscoelasticity value in the unified mesh within memory storage 948 in association with the vertex to which it pertains.

Figure 10:
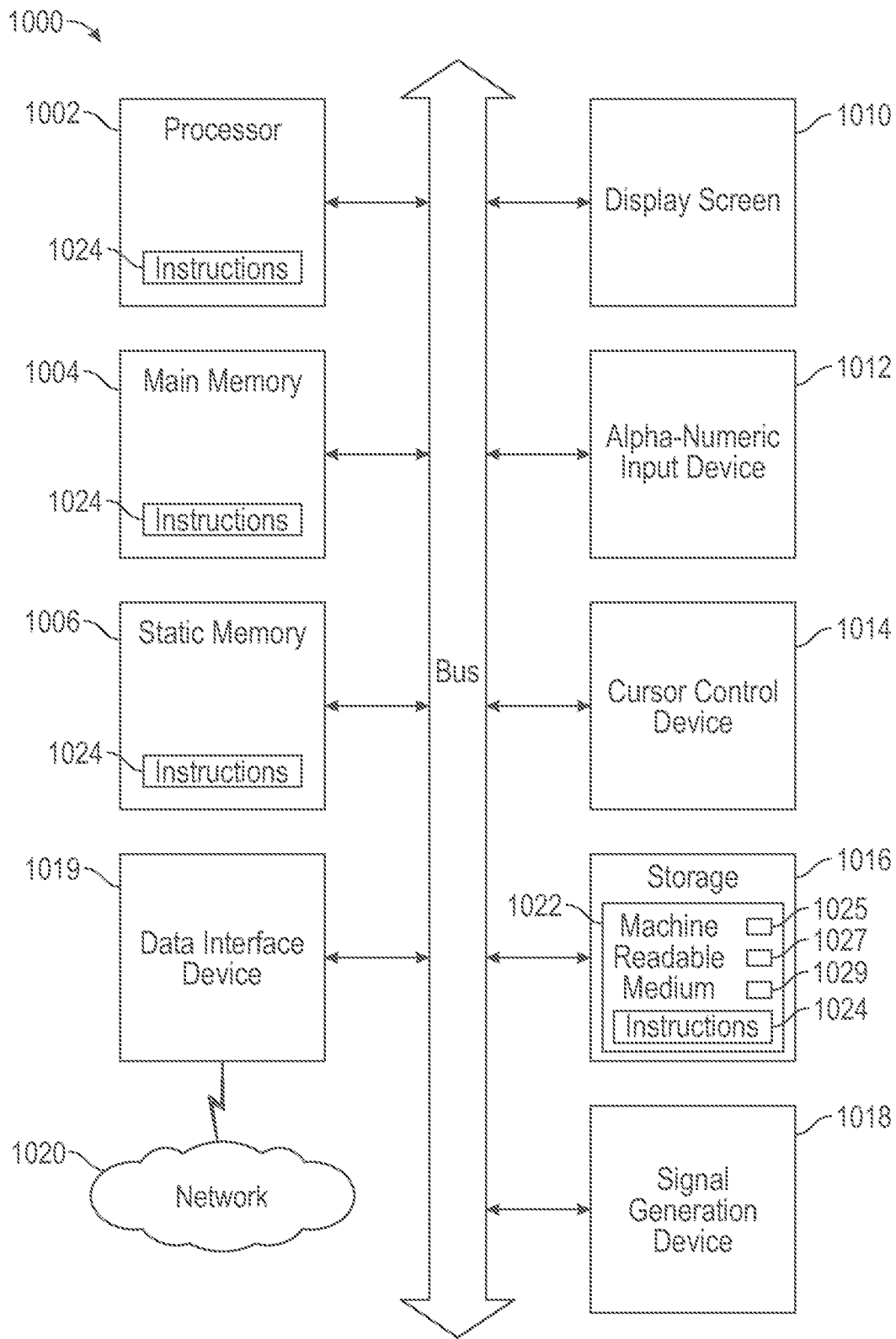
FIG. 10 is an illustrative diagrammatic representation of a computer system that may be configured to perform any one or more of the systems, engines, and methodologies discussed herein.

FIG. 10 shows an illustrative diagrammatic representation of a machine in the example form of a computer system 1000 within which a set of instructions is included, for causing the machine to perform any one or more of the methodologies discussed herein. In alternative embodiments, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a server computer, a client computer, a personal computer (PC), for example. Further, while only a single machine is illustrated, the term "machine" shall also be taken to include any collection of machines that individually or jointly execute a set (or multiple sets) of instructions to perform any one or more of the methodologies discussed herein.

The example computer system 1000 includes a processor 1002 (e.g., a central processing unit (CPU), a graphics processing unit (GPU), or both), a main memory 1004 and a static memory 1006, which communicate with each other via a bus 1008. The computer system 1000 may further include a display screen 1010 of a display device 112 (e.g., liquid crystal display (LCD), organic light emitting diode (OLED), touch screen, or a cathode ray tube (CRT)). The computer system 1000 also includes one or more user input devices to receive user input commands. The user interface input devices of the illustrative system include an alphanumeric input device 1012 (e.g., a physical or virtual keyboard), a cursor control device 1014 (e.g., a mouse, a touch screen, a touchpad, a trackball, a trackpad), a non-transitory storage device 1016, a signal generation device 1018 (e.g., a speaker) one or more data interfaces 1019 including an interface to a network interface device 120. The data interfaces 1019 may be wired or wireless to send and receive information such as motion picture camera image information or network information, for example.

The storage device 1016 includes a machine-readable medium 1022 on which is stored one or more sets of instructions 1024 (e.g., software) data structures 1025 (e.g., an index structure) embodying any one or more of the methodologies or functions described herein. The processor 1002 may be configured according to instructions 1024 in the machine-readable medium to act as a synthesis system 104, to act as a UMF conversion system 108, to act as a simulation engine 106 and to act as a shader engine 110. The machine-readable medium 1022 also may store 3D) image scan data model 116, a volume mesh representation 118, and a UMF representation 120. The storage device may include one or more of a disk drive, solid-state memories, optical and magnetic media, for example. The instructions 1024 may also reside, completely or at least partially, within the main memory 1004 and/or within the processor 1002 during execution thereof by the computer system 1000, the main memory 1004 and the processor 1002 also constituting machine-readable media. The instructions 1024, data structures 1025 and motion picture pixel frames 1027, 1029 may further be transmitted or received over the network 1020 via the network interface device 1019.

The above description is presented to enable any person skilled in the art to create and use a unified mesh format volume representation of a physical anatomical tissue structure. Various modifications to the embodiments will be clear to those skilled in the art, and the generic principles defined herein may be applied to other embodiments and applications without departing from the spirit and scope of the invention. In the preceding description, numerous details are set forth for explanation. However, one of ordinary skill in the art will realize that the circuitry might be practiced without the use of these specific details. In other instances, well-known circuits and processes are shown in block diagram form in order not to obscure the description of the invention with unnecessary detail. Identical reference numerals may be used to represent different views of the same or similar item in different drawings and in the specification. Thus, the foregoing description and drawings of embodiments in accordance with the present invention are merely illustrative of the principles of the invention. Therefore, it will be understood that various modifications can be made to the embodiments by those skilled in the art without departing from the spirit and scope of the invention, which is defined in the appended claims

What is claimed is:

1. A computer implemented method comprising:
identifying, by one or more processors, surface vertices and internal vertices of a volume mesh of an object;
organizing, by the one or more processors, the surface vertices of the volume mesh into a first sub-list of a list and the internal vertices into a second sub-list of the list;
using, by the one or more processors, a data structure identifying a base address pointing to the list, a count of the surface vertices in the first sub-list, and a count of the internal vertices in the second sub-list, to store the first sub-list and the second sub-list in a memory; and
using, by the one or more processors, the base address and the count of surface vertices to access in the memory the second sub-list of internal vertices.

2. The method of claim 1, further comprising using, by the one or more processors during shading of the volume mesh, the base address to access the surface vertices in the first sub-list.

3. The method of claim 1, further comprising using, by the one or more processors during simulation involving application of a virtual force to the volume mesh, the base address to access both the surface vertices in the first sub-list and the internal vertices in the second sub-list.

4. The method of claim 1, further comprising producing, by the one or more processors, the volume mesh of the object using primitive volumetric cells, the primitive volumetric cells include both the surface vertices and the internal vertices.

5. The method of claim 1, where the surface vertices define a surface mesh portion of the volume mesh and the internal vertices define vertices internal to the volume mesh.

6. The method of claim 1, wherein the first sub-list comprises locations of the surface vertices of the volume mesh and the second sub-list comprises locations of the internal vertices of the volume mesh.

7. The method of claim 1, wherein the first sub-list comprises a first ordered list of surface vertices and the second sub-list comprises a second ordered list of internal vertices.

8. The method of claim 1, where in the first sub-list of surface vertices precedes the second sub-list of internal vertices in the list.

9. A system comprising:
one or more processors coupled to memory, and configured to:
identify surface vertices and internal vertices of a volume mesh of an object;
organize the surface vertices of the volume mesh into a first sub-list of a list and the internal vertices into a second sub-list of the list;
store the first sub-list and the second sub-list in a memory using a data structure identifying a base address pointing to the list, a count of the surface vertices in the first sub-list, and a count of the internal vertices in the second sub-list; and
use the base address and the count of surface vertices to access in the memory the second sub-list of internal vertices.

10. The system of claim 9, wherein the one or more processors are further configured to access, during shading of the volume mesh, the surface vertices in the first sub-list using the base address.

11. The system of claim 9, wherein the one or more processors are further configured to access, during simulation involving application of a virtual force to the volume mesh, both the surface vertices in the first sub-list and the internal vertices in the second sub-list using the base address.

12. The system of claim 9, wherein the one or more processors are further configured to produce the volume mesh of the object using primitive volumetric cells, wherein the primitive volumetric cells include both the surface vertices and the internal vertices.

13. The system of claim 9, where the surface vertices define a surface mesh portion of the volume mesh and the internal vertices define vertices internal to the volume mesh.

14. The system of claim 9, wherein the first sub-list comprises locations of the surface vertices of the volume mesh and the second sub-list comprises locations of the internal vertices of the volume mesh.

15. The system of claim 9, wherein the first sub-list comprises a first ordered list of surface vertices and the second sub-list comprises a second ordered list of internal vertices.

16. The system of claim 9, where in the first sub-list of surface vertices precedes the second sub-list of internal vertices in the list.

17. A non-transitory machine-readable medium comprising instructions that, when executed by a computer system, cause the computer system to:
identify a volume mesh of an object, the volume mesh comprising surface vertices and internal vertices;
sort the surface vertices of the volume mesh into a first sub-list of a list and the internal vertices into a second sub-list of the list;
use a data structure to store the first sub-list and the second sub-list in a memory, the data structure identifying a base address pointing to the list, a count of the surface vertices in the first sub-list, and a count of the internal vertices in the second sub-list; and
use the base address to access in the memory one of the first sub-list of surface vertices or the second sub-list of internal vertices.

18. The non-transitory machine-readable storage medium of claim 17, comprising instructions to access, during shading of the volume mesh, the surface vertices in the first sub-list.

19. The non-transitory machine-readable storage medium of claim 17, comprising instructions to access, during simulation involving application of a virtual force to the volume mesh, both the surface vertices in the first sub-list and the internal vertices in the second sub-list.

20. The non-transitory machine-readable storage medium of claim 17, wherein the first sub-list comprises 3D locations of the surface vertices of the volume mesh and the second sub-list comprises 3D locations of the internal vertices of the volume mesh.

* * * * *